United States Patent [19]

Ginsburg

[11] 4,365,873

[45] Dec. 28, 1982

[54] SPATIAL FREQUENCY AND CONTRAST SENSITIVITY TEST CHART

[76] Inventor: Arthur P. Ginsburg, 132 Lonsdale Ave., Dayton, Ohio 45419

[21] Appl. No.: 282,997

[22] Filed: Jul. 14, 1981

Related U.S. Application Data

[63] Continuation of Ser. No. 98,084, Nov. 28, 1979, abandoned.

[51] Int. Cl.³ ............................................... A61B 3/02
[52] U.S. Cl. ...................................................... 351/239
[58] Field of Search ............................. 351/32, 36, 37

[56] References Cited

U.S. PATENT DOCUMENTS 2,385,992 10/1945 Jobe ...................................... 351/32
2,463,813 3/1949 Shepard ................................ 351/32

OTHER PUBLICATIONS

Ronchi, et al. Some Remarks on Ophthalmic Test Types, 1972.
Earle Brown, "Modern Optic" Reinhold Publishing Co., NY, 1965, p. 447.
Green et al., "Effect of Focus on the Visual Response to a Sinusoidal Modulated Spatial Stimulus", J. of Optical Society of America, vol. 55, No. 9, Sep. 1965, pp. 1154–1157.
Watanabe et al. "Spatial Sine-Wave Responses of the Human Visual System" Vision Res., vol. 8, 1968, pp. 1245–1263.
F. W. Campbell et al., "Optical & Retinal Factors Affecting Visual Resolution," J. Physiol., vol. 181, 4/65, pp. 576–593.
D. H. Kelly, "Stimulus Patterns for Visual Research" J. of Optical Society of America, vol. 50, No. 1, 11/60, pp. 1115–1116.
Westheimer, "Modulation Threshold for Sinusoidal Light Distributions on the Retina," J. Physiol., 1960, vol. 152, pp. 67–74.

*Primary Examiner*—John K. Corbin
*Assistant Examiner*—Rodney B. Bovernick
*Attorney, Agent, or Firm*—Donald J. Singer; Casimer K. Salys

[57] ABSTRACT

A chart and method for measuring and quantifying generalized visual sensitivity in terms of contrast sensitivity and spatial frequency response. The chart contains a multiplicity of grating patches whose contrast, in terms of luminance, varies sinusoidally for differing spatial frequencies. The threshold levels of contrast and spatial frequency at which the presence of gratings can be detected accurately defines generalized visual sensitivity.

17 Claims, 2 Drawing Figures

SPATIAL FREQUENCY AND CONTRAST SENSITIVITY TEST CHART

RIGHTS OF THE GOVERNMENT

The invention described herein may be manufactured and used by or for the Government of the United States for all governmental purposes without the payment of any royality.

This is a continuation of application Ser. No. 98,084, filed Nov. 28, 1979, now abandoned.

BRIEF SUMMARY

The invention is directed to a visual chart and a method of using that chart to evaluate the visual and/or optical system undergoing analysis in terms of both contrast sensitivity and spatial frequency response. The chart comprising a multiplicity of grating patches whose grating contrast, in terms of peak to trough luminance level, and spatial frequencies spans the visual and/or optical range of interest. The chart is scanned by the observer to determine the grating patches which lie at the threshold of detection.

These detection thresholds define the transfer function of the visual system, providing generalized visual sensitivity in terms of a relationship between contrast sensitivity and spatial frequency. In the case where an imaging electro-optical system is interposed between the chart and the observer, a quantitative measure of the system's spatial transmission characteristics is readily ascertained by noting degradation in the detection thresholds.

The grating forming each patch normally comprise alternating light and dark regions, varying sinusoidally between the extreme levels of luminance defined by the patch contrast. Generally, the spatial frequency of the gratings within any one patch remains constant.

DETAILED DESCRIPTION

As a prelude to a description of the invention and its embodiments, it is worth noting the contrast between testing techniques used to evaluate human sensory responses. In particular, note the disparity between testing of the visual and auditory senses. It is generally known that the standard auditory test consists of presenting a sequence of audio signals, which vary in both amplitude and frequency, to ascertain the threshold of audio sensitivity. On the other hand, conventional visual examinations singularly rely upon Snellen or similar type acuity charts, in near-total oblivion to the concurrent effects of contrast sensitivity and spatial frequency on visual sensitivity. Since the Snellen type acuity test consists of letters, typically L or E, set in a highly contrasted background, and these letters consist of luminance variations in terms of amplitude and spatial frequency over a very limited range, defined by the letter shape and size, it fails to adequately consider the functional relationship between contrast sensitivity and spatial frequency on visual sensitivity.

Advanced artisans have come to recognize the importance of the interrelationship between contrast sensitivity and spatial frequency in the visual process. Though the link is known, the difficulty in testing for these parameters in a simple, rapid, quantifiable manner has prevented widespread implementation. In those limited cases where outstanding visual performance is demanded, individuals are selectively tested for contrast sensitivity in relation to spatial frequency by varying patterns on TV type displays. The process is laborious and not readily amenable to comparison.

The invention disclosed and claimed overcomes these fundamental deficiencies in the art of testing and analyzing generalized visual acuity. It recognizes that the stimulus-response of a visual system is analogous to a filter function. The apparatus and method taught probes the visual system in terms of both contrast sensitivity and spatial frequency to arrive at their relationship, and does so in a quantifiable manner readily amenable to comparison and standardization. Central to the invention is the interrelationship of the patches within the chart, through which accurate measurements are rapidly obtainable.

Figure 1:
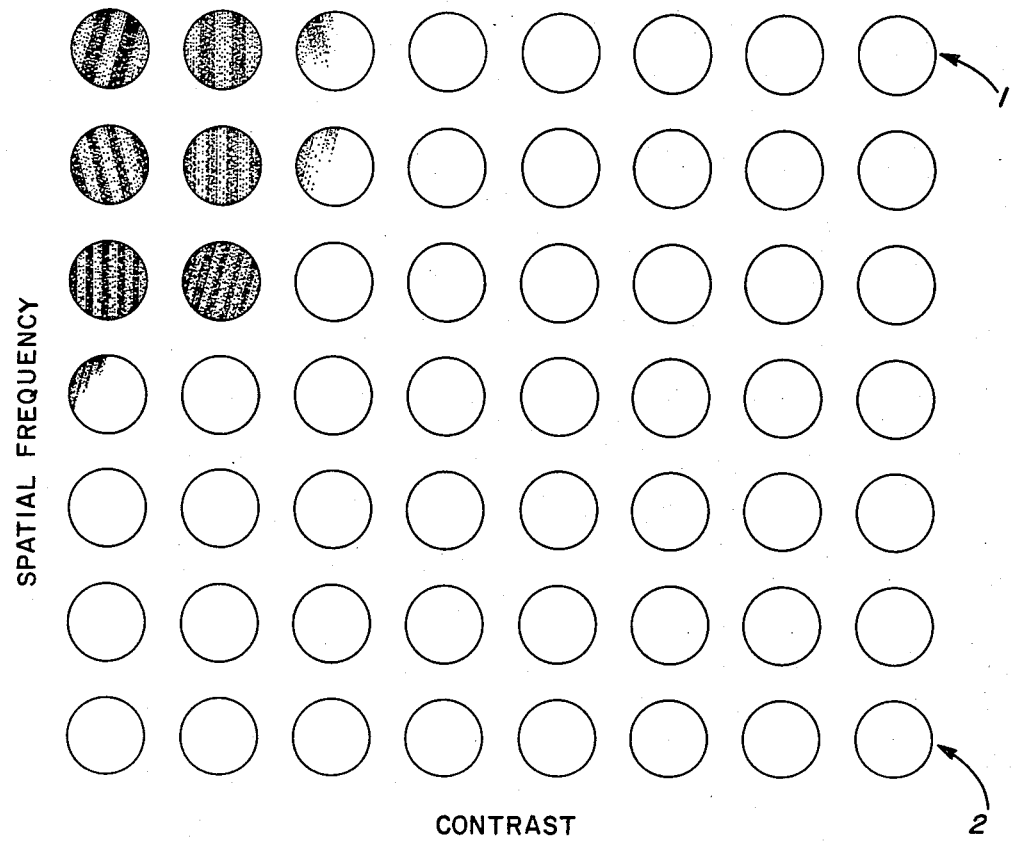
FIG. 1 schematically depicts an embodying chart specifically designed to test human visual sensitivity. The gratings in successive rows of patches increase spatial frequency by octave steps, while successive columns decrease contrast in half contrast increments.

Attention is now directed to FIG. 1 where one embodiment of the chart is schematically depicted. The shading and contrast levels of the patches appear more clearly in the photograph of FIG. 2, though the representations in this figure differ slightly in shape and organization from those in FIG. 1. Each patch in FIG. 1 contains a calibrated grating whose luminance level varies sinusoidally between the peaks of luminance. The patches themselves are systematically organized over the face of the chart such that the columns have equal contrast levels while rows have equal spatial frequency. As will become apparent from the forthcoming description, the contrast levels and spatial frequencies provided fully encompass the ranges of human perception.

The embodying visual sensitivity test chart depicted in FIG. 1 is approximately 61 cm (2 ft) high and 91.5 cm (3 ft) wide. Each grating patch is 7 cm (2.75 in) in diameter. The spatial frequencies covered by the chart range from 0.5 to 32 cycles per degree (cpd) in one octave steps (0.5, 1, 2, 4, 8, 16 and 32 cpd), from first row 1 to last row 2. Though spatial frequencies in excess of 32 cpd could have been included in this chart, those frequencies are usually below visual threshold under normal viewing conditions.

The term spatial frequency, as applied herein, contemplates cycles per degree based on the number of gratings per degree of visual angle subtended when observing the grating from a distance of one meter. As defined it is based on a small angular excursion. Clearly, the observation distance and grating size are inextricably linked when spatial frequency is presented in terms of cycles per degree.

Contrast is defined as functional relationship of maximum and minimum luminance levels using the equation:

$$C = (L_1 - L_2)/(L_1 + L_2),$$

where
$L_1$ = max. luminance
$L_2$ = min. luminance.

The level of contrast in the gratings of the embodying chart patches ranges from a maximum of approximately 15% to a lower bound of zero, progressing in half contrast steps from a maximum at the left edge of the chart. A practical upper limit for contrast is 30%. Greater levels do not exercise or probe the human visual faculty. In a like manner, the half contrast steps are merely preferred increments. If a larger chart is deemed acceptable, increments such as those related by $\sqrt{2}$ are readily amenable.

The shapes and orientations of the patches are also meaningful. For instance, the first patch, leftmost in row 1, is canted to the right by approximately 10 degrees, the second is vertical, while the next adjacent patch is canted approximately 10 degrees to the chart left. By reason of their circular shape, the observer must detect the orientation of the gratings to describe their direction. If the three patch orientations described are randomly distributed, the likelihood of a correct guess as to grating direction is reduced to 33%. Other techniques to avoid guessing biases are clearly foreseeable, for example randomly dispursed patches.

A further variation in the peripheral character of the patches is contemplated. Recognizing the potential biasing effects of an abrupt change in contrast between chart background and a luminous line at the edge of the patch, the contrast in each patch grating can be tapered to the background level at a Gaussian rate. In the second instance, the background of the chart can be shaded into correspondence with the average contrast level of the patch encircled.

Figure 2:
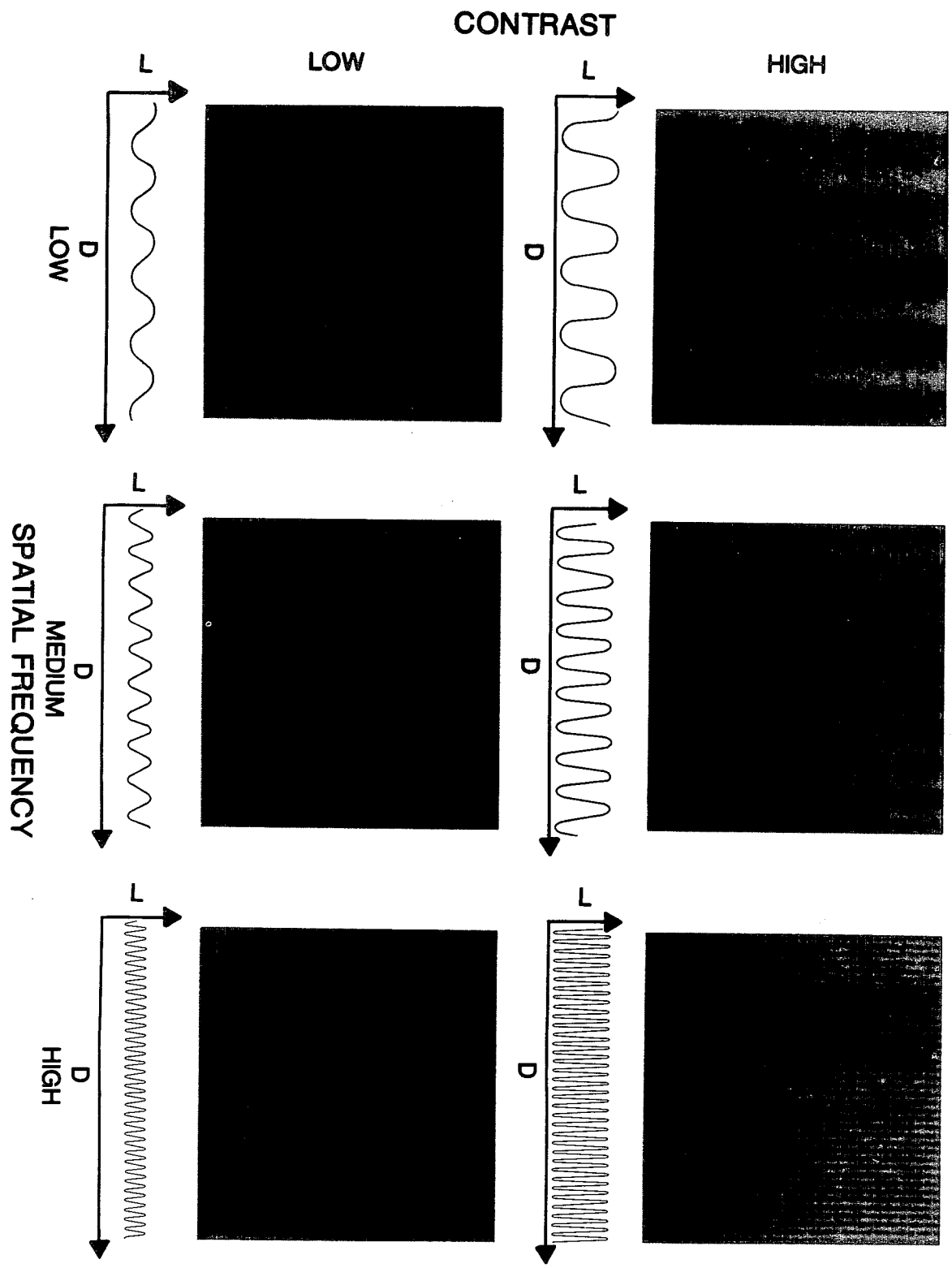
FIG. 2 of the drawings presents an accurate black and white photograph, in lieu of an India ink drawing, clearly showing the shading effects of the sinusoidal luminance variations. Beneath each of the six patches presented is a graph showing the interplay between contrast and spatial frequency.

The sinusoidal luminance and spatial frequency characteristics of sample gratings are visible in FIG. 2. It should be noted that the contrast and spatial frequency axes have been rearranged slightly for purposes of clarity. Beneath each grating patch is a plot of luminance verses displacement in direct correspondence to the pattern of the patch presented. The spatial frequency increases by factors of 2 and 8 moving from the lowest frequency, while contrast decreases by a factor slightly greater than 2 to 1 when moving from the high to the low contrast gratings.

The spatial frequency and contrast increments between the rows and colums in FIG. 1 are systematically defined from experiments and observations involving human visual characteristics. Octave stops of contrast and spatial frequency between rows and columns of patches are sufficiently small to detect variations in sensitivity, yet adequately large to reasonably limit the number in a chart. In general, the normal human visual system perceives variations within a two octave range.

As those skilled in the art may recognize, the above described apparatus and accompanying technique for its use provide the elements by which the spatial sensitivity of human visual system may be systematically probed. The products of such a probe are the quantifiable parameters of the transfer or filter function describing the visual system. These quantitative characeristics are readily amenable to modeling, for instance in attempting to ascertain the response of a complex imaging electro-optical system in which human visual sensitivity plays a part. Similarly, the chart provides a rapid means for evaluating the performance of electrooptical systems, by comparing direct observations of the chart with those obtained when the electro-optical device is interposed between the chart and the observer. In such a situation the same chart replaces conventional test charts, such as the Air Force Tribar or the RETMA.

In mathematical terms, each sine wave grating patch in the chart is a simple stimulus having a single amplitude and containing only one frequency. Since any complex object can be built up from a combination of spatial frequencies having different amplitudes and orientations, visual sensitivity as it relates to a complex object can be ascertained by noting the chart response. The results are analogous to those obtained when testing the human auditory system.

The use the visual test chart depicted in FIG. 1, the observer is situated at a distance of one meter from the chart. The chart is then scanned beginning in the upper left quadrant, proceeding to the right, by row, until the low contrast level, and then the high spatial frequency, prevents the observer from detecting the gratings or their orientation. The threshold levels are quantified and compared to a norm where optical or neurophysiological defects are being investigated. The same threshold data is useful in defining the transfer or filter function of the observer.

When the apparatus disclosed is utilized in the method described visual defects are detected which heretofore were not preceived with the Snellen or other conventional test techniques. A specific example is the case of an observer who complains of unequal quality of vision in one eye compared to the other while exhibiting substantially equal Snellen acuity in the two eyes. The unequal spatial frequency response of the two eyes is immediately apparent when the invention chart is used. This divergence in contrast sensitivity as spatial frequency decreases is a physiological phenomenon which cannot be detected by Snellen type charts. The high contrast of such charts is simply not sensitive to those differences at lower frequencies.

The invention disclosed herein contemplates further embodiments, varying both in structure and operation. Some examples are presented in the ensuing paragraphs.

Consider, as a first variant, the chart described with one or more supplemental rows of high contrast (square wave) grating patches, spanning a comparable frequency spectrum when observed from a distance of six meters. Recognizing that the human optical transfer function is substantially linear, these results may be compared to the other data for the purpose of verification.

In another approach for using the fundamental concepts disclosed, the spatial frequency range and test chart orientation are altered by changing the distance between the observer and the chart or by rotating the chart, respectively. To further avoid bias effects from adjacent patches, the frequency of the patch gratings may vary randomly over the face of the chart. Clearly, the method of detecting thresholds would vary correspondingly.

Further alternatives suggest square wave gratings of differing frequencies in place of the sine wave configuration described above, colored or moving grating patches, or patches having a consistent number of lines which are altered in spatial frequency by reducing the patch size. The latter is akin to the Snellen chart approach.

Also conceivable, as a variant to the embodiments described, are apparatus in which the chart as a whole, or by individual patches, is created or altered in spatial frequency and contrast by optical projections. A rudimentary example of this embodiment is a chart formed by projecting a transparency containing the grating patch chart onto a viewing surface.

More esoteric refinements of the invention encompass its use in quantitatively, accurately and rapidly evaluating the optical degradation attendant the taking of observations through an imaging electro-optical system. The invention is also amenable to probing different human retina locations in pursuit of evaluating peripheral vision characteristics.

The above are but a few of the many embodiments contemplated by the fundamental invention.

I claim:

1. A vision sensitivity evaluation apparatus by which the concurrent effects of contrast sensitivity and spatial frequency are ascertained, comprising:
   a visually perceivable chart having a multiplicity of patches being systematically organized over the face of the chart into a plurality of groups;
   each patch comprised by a grating of alternating light and dark regions being calibrated such that its contrast distribution varies between peaks and troughs of luminance and its pattern integrates a substantially constant contrast luminance level with a substantially constant spatial frequency;
   said gratings in one group of patches having substantially equal contrast levels which differ from the respective contrast levels of the gratings in other groups of patches;
   said gratings in a different one group of patches having substantially equal spatial frequencies which differ from the respective spatial frequencies of the gratings in other different groups of patches; and
   said grating of each patch having a particular perceivable orientation, depending upon the threshold of visual sensitivity of a normal observer, which renders its detection by the observer subject to verification.

2. The chart recited in claim 1, wherein the contrast luminance distribution varies sinusoidally at a constant spatial frequency on the grating of any one patch.

3. The chart recited in claim 1 or 2, wherein the spatial frequency band encompassed by the patches extends from about 0.5 to 32 cycles per degree in octave steps, and the contrast range decreases from a useful upper limit of about 30%.

4. The chart recited in claim 1, wherein said gratings of said groups of patches are arranged in successive columns which decrease in contrast level and in successive rows which increase in spatial frequency.

5. A method for determining the contrast and spatial frequency sensitivity of an optical and/or visual system, which comprises the steps of:
   successively observing a multiplicity of grating patches which vary in contrast and spatial frequency;
   identifying a particular perceivable orientation of each grating patch depending upon the threshold of visual sensitivity of a normal observer, which orientation renders its detection by the observer subject to verification; and
   ascertaining the grating detection threshold of the system for decreasing levels of contrast and increasing levels of spatial frequency.

6. The method recited in claim 5, wherein the grating contrast varies sinusoidally, the grating spatial frequency extends from about 0.5 to 32 cycles per degree in octave steps, and the patches range in contrast from a useful upper limit of about 30%.

7. The method as recited in claims 5 or 6, wherein the patches are observed through an optical imaging system and compared to the result in a direct observation so as to ascertain the degradation in contrast or spatial frequency sensitivity.

8. The chart recited in claim 1, wherein the grating of each patch is disposed at one of three possible orientations: canted to the right, substantially vertical, or canted to the left.

9. The chart recited in claim 1, wherein the alternating light and dark regions comprising the grating of each patch are substantially linear.

10. Vision sensitivity evaluation apparatus including means presenting a perceivable pattern of a multiplicity of distinctly separated patches, each of said patches comprising a grating embodying successively alternated light and dark regions, the elements of which have a substantially linear character and the contrast levels and/or frequencies of occurrence of which differ in different patches, said patches presenting a range of contrasting luminance and frequency of the occurrence therein of the alternated light and dark regions of their gratings, which upon observation by a person or system may be used as an accurate basis for determining the sensitivity and range of perception of that person or system to whom or to which the patches are presented for viewing.

11. Apparatus as in claim 10 wherein said patches are presented in groups and the degree of luminance contrast within the grating of each of said patches in one of said groups is essentially the same and differs from the degree of luminance contrast evidenced in the gratings of the patches in other of said groups.

12. Apparatus as in claim 10 wherein each said patch has the grating thereof embodying said successively alternated light and dark regions the elements of which are substantially linear in character so calibrated to present peaks and troughs of luminance across said regions in a repetitive sequence.

13. Apparatus as in claim 10 wherein the level of luminance in the grating of each of said patches varies sinusoidally in a direction transverse to the longitudinal extent of said substantially linearly configured elements thereof.

14. Apparatus as in claim 10 wherein said patches are arranged in rows and the patches of said rows are arranged to form a plurality of columns thereof and each of said columns exhibits in the patches forming the same a pattern of changing luminance across the gratings thereof which differs from that exhibited in the patches of the adjacent of said columns.

15. Apparatus as in claim 10 or claim 14 wherein said patches are arranged in rows and the said rows are arranged to form a plurality of columns of said patches and each of said rows has the patches thereof provided with gratings the frequency of the alternated dark and light regions of which differs from that of the gratings of the patches exhibited in adjacent of said rows.

16. Vision sensitivity evaluation apparatus as in claim 10 or claim 12 wherein said elements of the gratings of certain of said patches have a vertical orientation and the elements of the gratings of other of said patches have a degree of inclination from a vertical orientation in either a clockwise or counterclockwise direction with respect thereto.

17. Vision sensitivity evaluation apparatus as in claim 10 wherein said elements of each grating have a perceivable orientation by which they are distinguishable from the elements of other gratings.

* * * * *